July 20, 1937. P. L. LINGAMFELTER Plant Pat. 258

APPLE TREE

Filed March 4, 1937

Inventor
Paul L. Lingamfelter
By Robb & Robb
Attorneys

Patented July 20, 1937 Plant Pat. 258

UNITED STATES PATENT OFFICE

258

APPLE TREE

Paul L. Lingamfelter, Hedgesville, W. Va., assignor to Stark Bro's. Nurseries and Orchards Company, Louisiana, Mo.

Application March 4, 1937, Serial No. 129,075

1 Claim. (Cl. 47—62)

Figure 1:
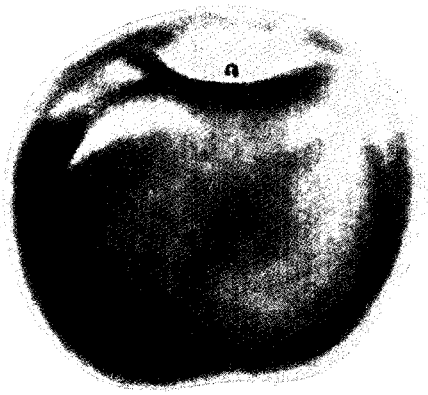

This discovery relates to a new and distinct variety of apple tree, the particular novel characteristic of which resides in its distinctive coloring.

The regular or well known variety of York Imperial (hereinafter called "York") apple is quite popular with the public at this time, but it has one important drawback, viewed from a commercial standpoint, and that is the lack of attractiveness of its color. For years nurserymen and orchardists have been searching for an apple which has the general characteristics of the York variety combined with a desirable red color, because of the added value and demand which such color gives to the apples, generally speaking. At the present time, certain red varieties springing from this York variety have become known, but the coloring materially departs from what may be termed the really attractive or interesting basic shade of red found all too sparingly in the genuine York.

The present discovery appears to fulfill the demand for the all-over uniform York red coloring, and notably lacks the purplish mahogany and bright cherry or pinkish red tinges of the prior York sports.

My discovery originated as a limb sport on a regular York apple tree in my orchards in Berkeley County, W. Va. The apples on this sport were conspicuously more highly colored than the fruit on adjoining limbs early in September. When viewed from the inside of the spread of the limbs, the fruit on this sport limb was practically as well colored on the inside as on the outside exposure, while the fruit on the rest of the tree, while fairly well colored at this date on the outside exposure, were still quite green on the inside exposure.

This uniformity and earliness of coloring is a very important factor, commercially speaking, because it permits growers to pick their apples while still hard ripe and yet get 100% all-over-red color, rather than resorting to the customary practice of leaving them on the tree until they become over-ripe, as is necessary to be done many seasons in order to get sufficient color on regular York apples.

My new all-over-red apple is approximately the same size and is similar in all other characteristics to the apples on the rest of the tree, the only difference being that my new variety of apple herein disclosed, two or three weeks before the apples on the rest of the tree begin to color, develops a deep, true York red color all over of the typical red that occurs basically in the ideally colored York, for which reason my new variety of apple can be picked when they are in crisp, hard-ripe condition in order to secure sufficient coloring for Grade No. 1.

One main distinction between my new variety of apple and that of the regular York is that in the case of the York only a few of the apples have even this partial ideal red coloring, whereas in the new variety all of the apples are so uniformly colored.

This color characteristic in the new variety is a very important factor to growers of York apples because good color is essential in order to secure the highest prices for their apples. Also this added color prevents scald in storage and gives the grower a longer keeping apple for storage purposes.

Figure 2:
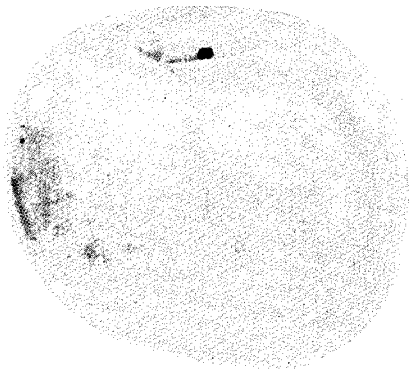

In the illustration annexed hereto, Fig. 1 shows my new variety of apple, and Fig. 2 shows the regular York variety of apple, by way of comparison of the color characteristics of the two varieties.

It will be obvious that the red coloring of my new variety corresponds to the basic red coloring of the regular York variety, but the coloring in the former is spread over the whole of the apple and is substantially uniform all over, as hereinbefore explained.

Since in all other characteristics of the apple tree my new variety corresponds to the regular York apple tree, it is deemed unnecessary to illustrate or describe the new variety in detail, reference being made to any well known text for such description. Asexual reproduction shows the new variety characteristics are fixed.

As a matter of convenience, the following technical description of the fruit of this variety is given:

Fruit, uniform in size and shape. Specimens tested seem to average with regular Yorks grown under same conditions.

Form is roundish oblate, sometimes truncate and usually with an oblique axis.

Shape is identical with York Imperial.

Stem, short and of medium thickness.

Cavity, medium, rather deep, often furrowed, usually somewhat russeted.

Calyx is small, usually closed.

Basin is usually large, abrupt, moderately deep, often furrowed.

Skin is tough, smooth, ground color yellow, entirely overspread with deep red. At picking time shows no stripes or blotches but has an even, uniform red color all over the apple and even into the basin.

Dots pale or russet.

Calyx tube elongated cone shape.

Core, medium in size, axile, the cells being symmetrical and core lines clasping.

Seeds, few, rather dark, wide and obtuse.

The flesh is yellowish, firm, crisp, breaking, somewhat coarse but moderately tender. Quite juicy.

Flavor is sub-acid, becoming mild as the apple matures. Slightly aromatic. Flavor seems to be identical with regular York.

Quality, good to very good.

I claim:

A new and distinct variety of apple tree characterized by its all-over-red coloring and the earliness in the season of such coloring, substantially as shown and described.

PAUL L. LINGAMFELTER.